United States Patent [19]
Williams et al.

[11] Patent Number: 5,330,916
[45] Date of Patent: Jul. 19, 1994

[54] CELLULAR COMPONENT EXTRACTION APPARATUS AND DISPOSABLE VESSEL USEFUL THEREIN

[75] Inventors: John G. Williams, Landenberg, Pa.; Louis G. Rosanio, Jr., Wilmington, Del.

[73] Assignee: E. I. du Pont de Nemours and Company, Wilmington, Del.

[21] Appl. No.: 830,389

[22] Filed: Feb. 3, 1992

Related U.S. Application Data

[63] Continuation of Ser. No. 543,928, Jun. 26, 1990, Pat. No. 5,114,858.

[51] Int. Cl.$^5$ .................... C12M 1/12; C12M 1/24; C12M 1/36
[52] U.S. Cl. .................... 435/311; 435/296; 435/289; 422/101; 210/321.63
[58] Field of Search ............ 435/270, 287, 296, 302, 435/311, 312, 289; 422/101, 102, 61, 64, 63, 212, 211, 239, 270–273; 436/174, 177; 935/19, 20, 21; 536/28, 72; 100/113, 131, 110, 134, 213, 211

[56] References Cited

U.S. PATENT DOCUMENTS

| | | | |
|---|---|---|---|
| 2,018,932 | 12/1933 | Thorne | 100/213 |
| 4,800,020 | 1/1989 | Savas et al. | 422/101 |
| 4,837,159 | 6/1989 | Yamada | 422/64 |
| 4,891,134 | 1/1990 | Vcelka | 422/101 |

*Primary Examiner*—Robert J. Warden
*Assistant Examiner*—T. A. Trembley
*Attorney, Agent, or Firm*—Jane E. Obee

[57] ABSTRACT

A method of extracting cellular components, e.g., nucleic acids, particularly DNA, from biological, especially solid tissue, samples, particularly from plants, is provided, whereby all of the steps can be performed in one vessel, and the entire process can be automated. A vessel suitable for this process is provided, as well as a system for the automated performance of the process steps.

6 Claims, 8 Drawing Sheets

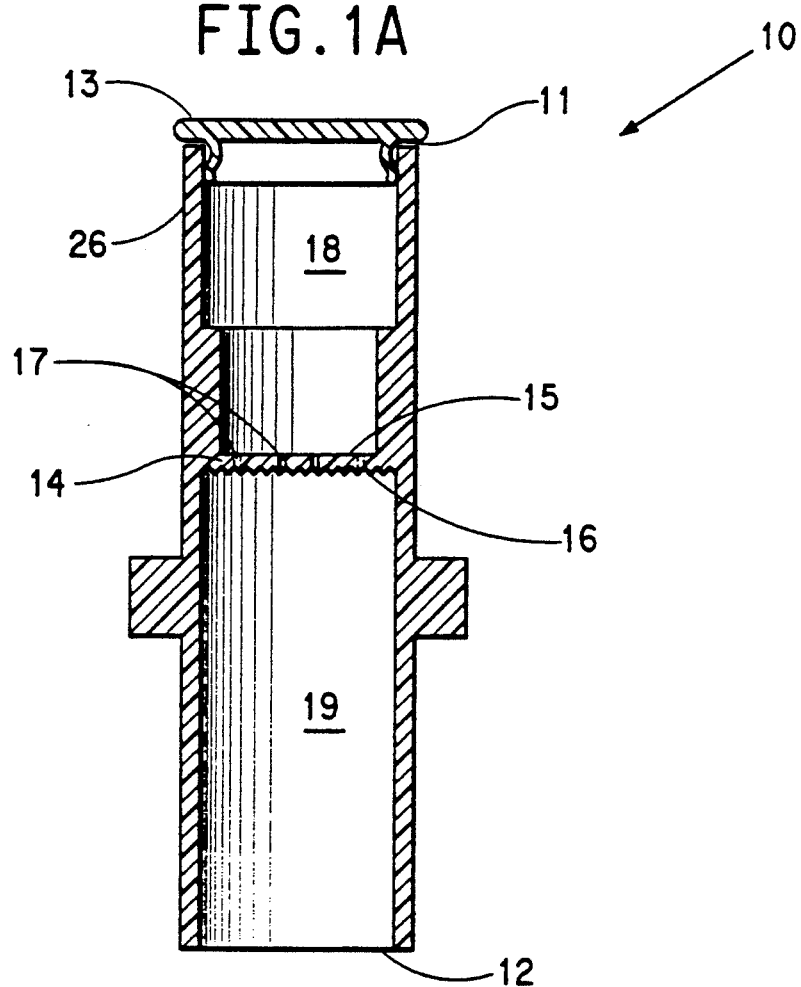
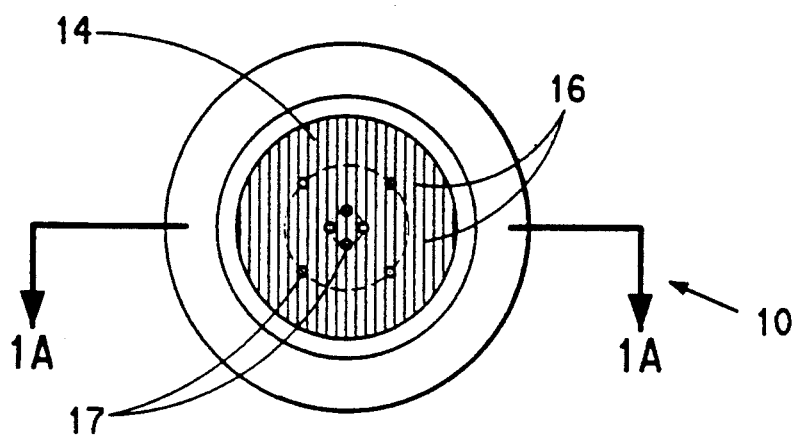

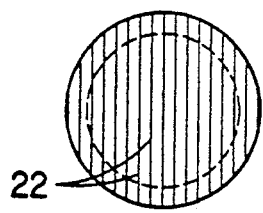
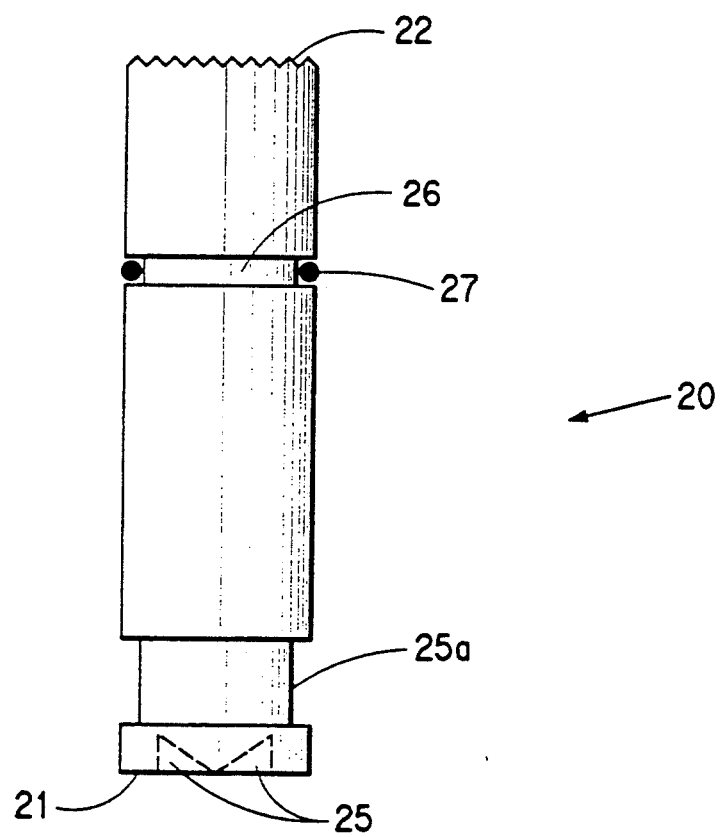
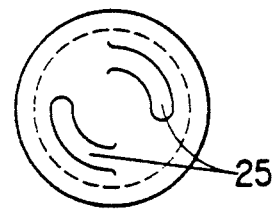

|  | LYOPH. MAIZE | | FRESH SOY | | LYOPH. RICE | |
|---|---|---|---|---|---|---|
|  | #1 | #2 | #3 | #4 | #5 | #6 |
| TOTAL ug DNA | 19.60 | 21.00 | 8.90 | 4.30 | 13.20 | 14.20 |
| TOTAL NUCLEIC ACIDS (ug) | 195.00 | 204.00 | 104.00 | 64.00 | 75.00 | 70.00 |

CELLULAR COMPONENT EXTRACTION APPARATUS AND DISPOSABLE VESSEL USEFUL THEREIN

This is a continuation of application Ser. No. 07/543,928 filed Jun. 26, 1990, now U.S. Pat. No. 5,114,858.

BACKGROUND OF THE INVENTION

The purification of DNA to a degree of purity suitable for further use, for example, amplification or processing with restriction enzymes, probe hybridization, cloning and so forth, is a well-known procedure (See, e.g., M. Ausubel et al., Eds., *Current Protocols in Molecular Biology*, Chapter 2, Section I.1-I.4, Wiley, 1989). These procedures lend themselves to rapid processing and automation, so long as the source of the DNA does not require physical grinding or maceration to disrupt cells or tissue; for example, DNA from biological fluids.

A need therefore exists to rapidly and reliably purify DNA from sources that require grinding or maceration to release DNA into solution (hereinafter referred to as "solid samples" for brevity). These samples, e.g., from plant, animal or microorganism sources, leave insoluble tissue or cellular material as by-products of the purification process.

The purification of DNA from these sources is considerably more difficult and time-consuming than from biological fluids, since another phase separation step (the solid from the liquid phases) is needed (see M.W. Lassner, P. Peterson and J.I. Yoder *Plant Molecular Biology Reporter*, 72, 112-128 (1989). Techniques for automating such processes are lengthy and normally employ centrifugation to separate phases. These requirements have prevented the development of commercially viable, fully automated protocols for the purification of DNA from plants, animals and microorganisms when mechanical disruption is needed to release DNA from the samples.

SUMMARY OF THE INVENTION

This invention relates to a process of isolating subcellular components, especially nucleic acids, e.g., DNA, from a biological sample, particularly a solid tissue sample, employing a novel filtration/reverse-filtration step after maceration or grinding, if necessary, of a solid sample, whereby centrifugation of the extraction mixture to separate cellular debris can be eliminated, and the number of overall steps heretofore required is dramatically reduced. Moreover, the process of this invention is efficient enough to permit reliable and rapid automated processing of large numbers of samples. In addition, the process can be easily adapted to isolate essentially any subcellular components of such biological samples. Furthermore, this invention also relates to a system that is particularly useful for purifying cellular components such as nucleic acids, e.g., DNA, from solid samples using said process, and a vessel that is particularly useful in said system.

Thus, this invention provides a method of separating nucleic acids from a biological sample, comprising:
(a) breaking open cells of the sample;
(b) separating aqueous solvent-soluble components of the cells into one phase and organic solvent-soluble components of the cells into a second phase, in the first compartment of a vessel assembly comprising two compartments separated by a filter;
(c) filtering the aqueous phase into said second compartment through a filter having a first side and a second side, such that said aqueous solvent phase is on the first side of said filter and said organic solvent phase and any cellular debris is on the second side of said filter;
(d) precipitating nucleic acids out of the aqueous phase in the second compartment of the vessel; and
(e) filtering the precipitated nucleic acids onto the second side of said filter in the second compartment of the vessel, the filtrate passing through the filter.

In a preferred embodiment, the nucleic acid is DNA.

More generally, this invention provides a method of fractionating cellular components of a biological sample, comprising
(a) breaking open cells of the sample;
(b) separating (a) aqueous solvent-soluble components of the cells into one phase and/or (b) organic solvent-soluble components of the cells into a second phase, in the first compartment of a vessel assembly comprising a first and a second compartment;
(c) filtering the aqueous phase into said second compartment through a filter having a first side and a second side, such that said aqueous phase is on said second side of said filter and said organic phase and any cellular debris remains on said first side of said filter; and
(d) separating onto the second side of the filter a desired cellular component from undesired cellular components.

The invention further provides a vessel assembly for storing, transporting and/or processing biological samples from which cellular components such as nucleic acids are extracted, comprising:

an extraction vessel having an upper chamber and a lower chamber, the chambers being separated by a radially extending wall with means for allowing fluid to pass therethrough, the upper chamber and lower chamber of the extraction vessel having openable ends;

a plunger means for insertion into the lower chamber, and means for retaining the plunger means in the lower chamber to retain said sample between the plunger means and wall;

means associated with the plunger means and wall for disrupting the sample upon relative movement between the vessel and sample, whereby nucleic acids inter alia are released therefrom, and means for sealing between the plunger means and the lower chamber to block fluid communication of the released nucleic acids and/or other cellular components through the lower chamber openable end.

In a preferred embodiment, the vessel assembly further comprises a tube means having a barrel, the tube means insertable into the upper chamber for accumulating the, for example, nucleic acid-containing fluid introduced therein from the lower chamber, the tube means further including means for separating soluble from insoluble material in said fluid upon transfer of said fluid from the upper chamber to the barrel of the tube.

The invention further provides an apparatus for automatically extracting nucleic acids or other cellular component from biological samples which apparatus utilizes the above-mentioned vessel assembly, the apparatus comprising in combination with the assembly;

a turntable having port stations with a first array of ports circumferentially distributed therearound for receiving the extraction vessels without the filter tubes inserted therein and a second array of ports distributed circumferentially therearound in radial alignment with the first ports for subsequently receiving the filter tubes;

means for inserting the extraction vessels in the first ports;

means for inserting the filter tubes in the upper chambers of the extraction vessels;

means for removing the filter tubes from the extraction vessels and inserting the filter tubes in the second ports radially adjacent the first ports;

means for removing both the extraction vessels and filter tubes from the turntable after separating the nucleic acid or other material extracted from the biological sample; and processing means associated with at least one station for processing the sample at said station.

Upon further study of the specification and appended claims, further objects and advantages of this invention will become apparent to those skilled in the art.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein:

FIG. 1A is an sectional view taken along lines 1A—1A of FIG. 1B of a double-ended extraction vessel configured in accordance with the principles of the instant invention for containing a solid tissue sample;

FIG. 1B is a bottom end view of the vessel of FIG. 1A;

FIG. 2A is a side view of a grinder-plunger which is assembled with the vessel of FIGS. 1A and 1B;

FIG. 2B is top end view of the plunger of FIG. of 2A showing a serrated surface;

FIG. 2C is a bottom end view of the grinder-plunger of FIG. 2A showing a rotational drive coupling;

FIG. 3B is a cross-section taken along lines 3B—3B of FIG. 3a;

DETAILED DESCRIPTION OF THE PREFERRED EMBODIMENT

As an overview, the process of this invention generally comprises first disrupting a biological sample, particularly a solid sample, of, e.g., plant or animal tissue, e.g., by mechanical grinding or maceration, in the presence of an aqueous extraction buffer in one compartment of a vessel assembly containing at least two compartments. In the case where the tissue sample has been previously dehydrated, e.g., lyophilized, the sample is preferably first rehydrated, e.g., in the extraction buffer prior to disruption, which significantly enhances nucleic acid yield. The disrupted tissue is incubated in a mixture of the extraction buffer and an organic solvent, e.g., chloroform, which is immiscible with the aqueous phase. The two liquid phases of the extraction mixture are then allowed to separate, and the aqueous phase is then passed through a filter into a second compartment of the vessel assembly to remove particulates. Care is taken to filter only the top aqueous phase; the bottom solvent phase is left behind at this step.

With respect to a preferred aspect of this invention involving nucleic acid extraction, a nucleic acid precipitant such as an alcohol, e.g., isopropanol, is then added to the aqueous filtrate to precipitate the nucleic acids. The remaining solution is then removed by passing the sample back through the same filter, leaving the nucleic acids in the second compartment of the vessel assembly and passing the filtrate back into the first compartment. A washing solution can then optionally be passed over the precipitate on the filter to further wash the precipitate. Finally, the nucleic acid precipitate is recovered by dissolving it in an aqueous solvent.

The isolated nucleic acids generally consist of about 90% RNA and 10% DNA. The purity of the DNA is such that, e.g., it can be amplified or can be cut with restriction enzymes. The purity of the nucleic acids is thus sufficient for, e.g., amplification, e.g., by PCR, screening for the presence or absence of a particular DNA sequence, locating the site of insertion of an engineered gene sequence, creating cDNA libraries from the RNA, Southern blot hybridization for the detection of particular DNA sequences, isolating DNA for subsequent cloning and/or sequencing, etc. Other uses for the products of this invention are fully conventional, and are well-known to one of ordinary skill in the art.

Figure 5:
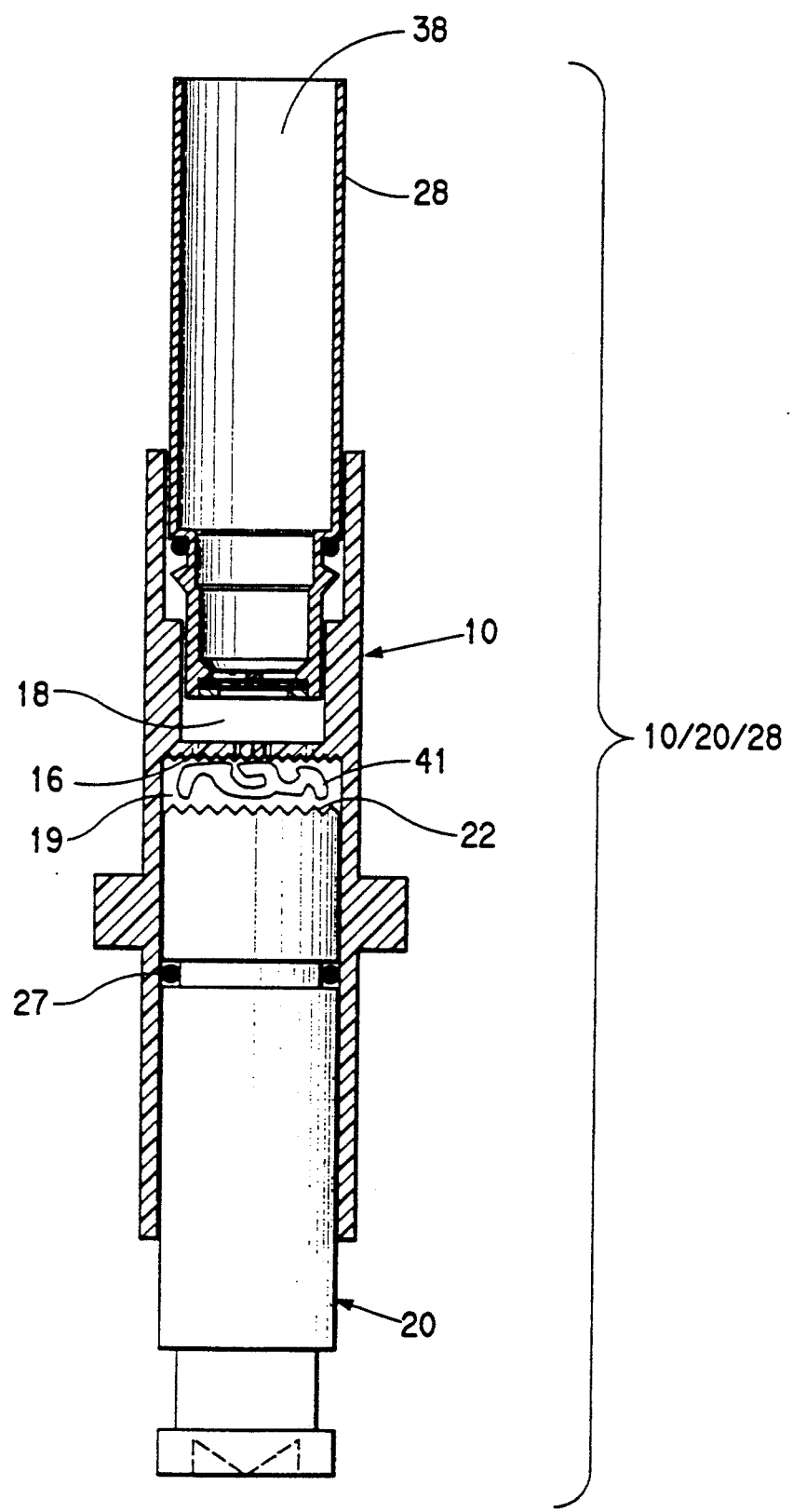
FIG. 5 is a side section view of a vessel assembly showing the extraction vessel of FIG. 1A in combination with the grinder-plunger of FIG. 2A and the filter tube of FIG. 3A.

The process of the instant invention is preferably performed in the vessel assembly of FIG. 5. The full process can be performed in as few as 8 steps, with no steps requiring manual transfer of solutions between vessels, centrifugation, etc., so that the process can be fully automated.

In the process described below, reference is made to the various components of the vessel assembly which is also a subject of this invention. However, it is understood that one of ordinary skill in the art could easily and routinely substitute related and/or equivalent means for performing the steps described below for achieving substantially the same result. Therefore, the process as described below is but one embodiment of a process which can be achieved by other means, but which are within the scope of this invention. The particular advantages of this process are best achieved, however, when most if not all of the steps are performed within a single vessel, and when the two filtering steps are performed in opposite directions on a single filter. Thus, although the method describes two compartments separated by a filter, when the vessel assembly of this invention is employed, which assembly is particularly suitable for extracting nucleic acids from solid tissue samples without transfer to other vessels, the first compartment referred to in the method corresponds to the combined two chambers in the extraction vessel, which communicate through holes in the partition, and the second compartment corresponds to the space within the barrel of the filter tube.

It is further noted that, although the preferred embodiment of the method of this invention is the isolation of nucleic acids, in particular DNA as mentioned, it is well within the skill of one of ordinary skill in the art to also utilize this invention as a general method of isolating various cellular materials, in particular, the non-nucleic acid aqueous soluble components of the cell, the organic solvent-soluble components of the cell or the insoluble components of the cellular debris from, respectively, the filtrate from the nucleic acid precipitate, the organic solvent phase, or the cellular debris. This can readily be accomplished by using the apparatus and devices of this invention in conjunction with conventional reagents and process conditions which, in combination with the manipulation of the apparatus and devices of this invention in analogy to the manipulations exemplified herein, can effectively and selectively separate the desired component from the undesired components.

Except for the optional heat treatment in step 4, each of the following steps can be conducted at about room temperature, although any temperature in the range of about 0°-37° C. is acceptable. If integrity of the eluted nucleic acids is critical, variations in the following process, well known to one of ordinary skill in the art, can be employed, e.g., performing the steps with little delay after extraction, performing the process at cold temperatures, addition of RNAase or DNAase inhibitors, etc.

The term "biological sample" as used herein refers to any material comprising or derived from a living or once-living organism, including viruses, bacteria, yeasts, fungi, plants and animals including humans. In the process steps described below, reference is made in particular to the extraction of solid tissue samples. However, it will be evident to one of ordinary skill in the art that this process is equally applicable to biological samples which are not solid, such as, e.g., blood cells, bacterial cultures, previously disrupted samples, etc., with or without the use of some of the particular components, e.g., the plunger-grinder, of the vessel assembly described below.

In the first step, a tissue sample is placed in an extraction vessel, e.g., of the type of the instant invention. Between 0.005 and 5.0 g of tissue is typically used, preferably about 0.5 g. When the extraction vessel of this invention is used, the sample is placed into the lower chamber 19, which is separated from the upper chamber 18 by a partition 14 containing holes 17, which acts as a frictional surface for disrupting the tissue and as a coarse filter for the aqueous extract. A means for disrupting the tissue, e.g. a grinder-plunger 20 which securely fits into the lower chamber 19 and which has a surface 22 having a means for disrupting the tissue, is inserted into the lower chamber 19 of the extraction vessel. If the sample is to be extracted immediately, the next step is performed at once. Otherwise, the plunger can be fitted into the lower chamber without crushing the tissue and acts as a plug until the sample is to be extracted. If the sample is not to be extracted within a short period of time, e.g., the same day, the sample may be lyophilized or frozen for longer-term storage. Alternatively, of course, if the sample is not to be extracted immediately, another type of plug may be employed to secure the sample in the vessel, and the plunger fitted into the vessel at the time of extraction. Also alternatively, the sample can be collected, lyophilized, transported, and/or disrupted in a different container. The vessel containing the sample will preferably be labelled; this labelling is preferably effected by use of a machine-readable label so as to facilitate the automation of the succeeding steps, and to prevent mix-ups.

In the second step, an aqueous extraction solvent is added to the sample. The extraction solvent can be any aqueous solution in which the nucleic acids are both soluble and stable; for example, the CTAB extraction buffer of Lassner et al., supra, is preferred. Other suitable aqueous solvents can routinely be determined by one of ordinary skill in the art. Simultaneously with, just prior to or immediately after the disruption of the cells described below, an aqueous extraction solvent, e.g., an aqueous buffer, is added to the tissue sample or the previously disrupted cellular pulp. When the vessel assembly of this invention is used, the solvent can be added, e.g., by placing the buffer in the upper chamber 18 and withdrawing the grinder-plunger 20 a distance sufficient to draw the extraction buffer into the lower chamber 19. In particular, if the tissue sample was lyophilized prior to the extraction, it is preferably rehydrated, e.g., under conventional condictions. For example, it is preferably allowed to soak in the extraction buffer a sufficient time, e.g., about 6 min., in order to rehydrate the sample. The preferred volume of extraction buffer is about 4 ml, in the case of the dimensions of the preferred vessel assembly, in order to have a volume that is conveniently handled in later steps of the process. For other sizes and configurations of vessel assemblies and other volumes of tissue, one of ordinary skill in the art can routinely optimize these conditions.

The tissue sample is generally disrupted in the third step. Note, however, that the extraction solvent may also be added after the tissue sample is disrupted without significantly affecting the outcome of the process, if the sample contains sufficient fluid to allow the sample to be efficiently disrupted. When the vessel of this invention is employed, first the disruption means, e.g., the surface of the grinder-plunger 22 is applied to the tissue, such that the cells of the tissue are substantially disrupted, e.g., crushed and/or ground, against the vessel partition, releasing intracellular contents. The plunger is pushed all the way into the lower chamber until it is abutting the vessel partition, with the sample disposed between the plunger and the partition, and the plunger is then rotated in a single direction or in both directions, while maintaining a constant pressure on the sample. Using the grinder-plunger of this invention, a leaf sample of 0.5 g is generally completely disrupted within 15 sec. However, any other means of disrupting the cells, in particular a means which is amenable to automation, may be substituted for the plunger or other mechanical grinding means of this invention, e.g., a sonicator.

After the tissue sample is completely disrupted in the extraction solvent, an aliquot of organic solvent is added to the buffer/aqueous solvent/disrupted tissue sample mixture. This solvent is preferably chloroform, but any organic solvent which is immiscible in the aqueous solvent, which solubilizes e.g., hydrophobic proteins and cellular lipids, and which does not have an adverse effect on the nucleic acids or on the subsequent partitioning step, is suitable, e.g., phenol. The amount of organic solvent will vary with its properties, with dimensions of the device of this invention, with the cellular components involved, etc., but will generally be from 0.1 to 1.0 ml, preferably 0.4 ml when the organic solvent is chloroform and the amount of the aqueous solvent is 4 ml. The buffer/aqueous solvent/disrupted tissue sample mixture is then thoroughly mixed with the chloroform in order to extract the organic-soluble components from the aqueous solvent phase.

When using the vessel assembly of this invention, the organic solvent is conveniently added to the top chamber of the extraction vessel and is drawn into the lower chamber by withdrawing the plunger an appropriate distance. The mixture is completely mixed with the organic buffer by pushing the plunger in and out one or more times, with the final position determined so as to just draw all of the sample out of the top chamber and into the lower chamber. Other means of mixing the solvents with the disrupted tissue sample are also possible.

In the fourth step, the disrupted tissue is incubated with the aqueous and organic solvents for routinely determinable time periods, e.g., 1 to 20 min. Preferably, although not necessarily, this incubation step is carried out at elevated temperatures sufficient to inactivate cellular enzymes; for example the incubation can be carried out at temperatures between about 20° to 100° C. Preferably, the incubation step is carried out at about 65° C. for about 5 min. When the vessel assembly of this invention is used, the mixture is forced into the upper chamber 18 of the extraction vessel by pushing the plunger all the way into the lower chamber 19, abutting the partition, after the incubation period is complete. After the incubation period, the sample is allowed to sit undisturbed for a sufficient time, e.g., at least two minutes, to allow for partitioning of the organic and aqueous solvent phases.

In the fifth step, after the aqueous solvent phase has partitioned from the organic solvent phase, wherein the organic phase settles below the aqueous phase, any remaining particulate matter is removed from the aqueous extract by filtration. A filter tube 28 of pore size 0.2 to 10 μm, preferably 1 μm, such as a Uniprep filter (Genex Corp.), is inserted into the top chamber 18 of the vessel assembly while holding the plunger 20 firmly against the partition 14 between the chambers. This causes the aqueous extract phase to pass through the membrane 33 of the filter into the barrel 38 of the filter tube. It is understood that any other suitable filtration means can be interposed into a suitable vessel assembly for the same purpose of separating the organic phase and cellular debris into a first compartment of the vessel assembly by filtering the aqueous phase into a second compartment, and would be a routine variation for one of ordinary skill in the art. The filter tube 28 is pushed into the upper chamber 18 of the vessel assembly of this invention far enough to filter the aqueous phase into the barrel 38 of the filter tube while avoiding contact with the organic phase. Other equivalent means of filtering the aqueous extract through the filter can readily be envisioned by one of ordinary skill in the art, such as, e.g., gently forcing the aqueous phase from below with, e.g., the grinder-plunger or by air pressure, up to a filter already in place; applying negative pressure from the opposite side of a filter already in place; etc., each of these means to be considered fully equivalent of the process as set forth herein.

In the sixth step, the nucleic acid is precipitated e.g., by creating a homogeneous mixture of the aqueous phase and a nucleic acid precipitant, e.g., isopropanol or other conventional precipitant, in the upper compartment of the vessel assembly. The volume of precipitant added is that which is required to precipitate the majority of the nucleic acids present in the extract; in the case of isopropanol, it will typically be at least 0.6 times the volume of the filtrate. Other suitable nucleic acid precipitants include other organic solvents, e.g., ethanol or acetone, which are suitably miscible with water and cause precipitation of nucleic acids dissolved in the aqueous solvent, especially the DNA. Another advantage of the alcoholic precipitant is that it assists is removing turbidity associated with the lysate filtered through the filter.

In the seventh step, the liquid portion of the precipitated nucleic acid/aqueous solvent/nucleic acid precipitant is passed out of the barrel of the filter tube, back through the reverse side of the same filter, and into the extraction vessel. This may be accomplished by any suitable means, e.g., vacuum applied from below, or, preferably, by applying pressure, e.g., air pressure, of suitable force, e.g., less than 100 psi, to the top of the filter tube barrel. The precipitated nucleic acid is thus trapped on the top, i.e., second side, of the filter.

The eighth step, which is optional, depending upon the use for which the nucleic acids are being isolated, is to wash the precipitated nucleic acid sample free of any remaining impurities such as, e.g., salts and/or detergents from the aqueous solvent. The wash solution, e.g., a 70:30 solution of ethanol:water or any other solution conventionally designed with respect to the systems of interest, can be introduced into the barrel of the filter tube through the open end and forced or suctioned through the precipitate on the filter as in step 7.

In the ninth step, the nucleic acids are eluted from the filter. Any method of solubilizing the nucleic acids which is compatible with the materials from which the extraction vessel and filter tube are made and the subsequent use of the nucleic acids is suitable. The preferred method is add at least 0.1 ml of a solution in which the nucleic acids are soluble, e.g., Tris-EDTA (= TE; = 10 mM Tris-Cl, pH 7.5, 0.1 mM EDTA), directly to the barrel of the filter tube and applying positive pressure, e.g., 10 psi, to the barrel of the filter, or negative pressure at the open end of the filter, to force the solution and dissolved nucleic acids through the filter membrane to the open end of the filter, from where the solution is collected. A variation of this method is to force at least 0.1 ml of Tris-EDTA from the open end of the filter into the barrel of the filter using either positive pressure at the open end of the filter or negative pressure in the barrel of the filter, and collecting the dissolved nucleic acids from within the barrel of the filter. A third possibility is to soak the filter for a sufficient length of time and then directly remove, e.g., by pipetting, the eluate from the surface of the filter, thereby avoiding the use of forced air. A fourth possibility is to remove the filter tube from the vessel assembly, dissolve the nucleic acids in a liquid (either before or after removing the filter tube from the assembly), and apply air pressure to the top open end of the filter tube, forcing the dissolved nucleic acids back through the filter and into a collection means.

Although extraction of DNA is a preferred embodiment of this invention, it will be evident to one of ordinary skill in the art that other cellular components also may be readily prepared utilizing this extraction method and the device/apparatus of this invention in analogy to the discussion herein. Thus, the nucleic acids obtained by this technique include both DNA and RNA, and RNA may be isolated from the precipitate by fully conventional techniques.

Furthermore, the technique of this invention may be adapted to isolate other desired non-nucleic acid components of the cells. For example, the filtrate which passes through the filter in step seven contains the aqueous solvent-soluble proteins, as well as other aqueous-solvent soluble material, which were co-extracted with the nucleic acids. These proteins may be isolated from the filtrate by fully conventional techniques well-known to one of ordinary skill in the art, e.g., selectively precipitating with ammonium sulfate, or by binding of protein selectively with a specific antibody followed by the addition of the usual adjuvants for rendering the protein-antibody complex insoluble. This selective precipitation may also be applied in the case of other aqueous solvent-soluble components, e.g., small molecules which may also be precipitated using the antibody binding technique. The term "selectively precipitating" as used herein is most general, e.g., meaning that the concentration of the desired component in the precipitate is enhanced over that of the other components compared with its concentration in the aqueous phase from which it is precipitated. Preferably, of course, the precipitate will contain essentially only the desired component. It is further noted that the extraction conditions, in particular the buffer solutions and times of extraction, may be optimized by one of ordinary skill in the art using only routine experimentation and/or routine knowledge.

Still further, the organic solvent phase will contain other cellular materials which may be of interest in particular applications; for example, the lipid profile of the cells may be determined by analysis by fully conventional techniques, such as, for example, high performance liquid chromatography or gas chromatography. The components of the organic phase may be isolated after the aqueous solvent-soluble components are separated or instead of the aqueous solvent-soluble components. Thus, using the method of this invention, after the aqueous phase has been filtered into the second compartment of the vessel, the aqueous phase can be removed from the compartment, e.g., by pipetting the liquid out. It is also noted that the aqueous phase may or may not have already been subjected to the selective precipitation steps discussed above. The organic phase can then be filtered into the second compartment, and the organic solvent-soluble components can then be separated, e.g., from the organic solvent, onto the filter by means well known to one of ordinary skill in the art, e.g., crystallization, evaporation of the organic solvent, etc. It is noted also that for certain applications, further separation of the components from the solvent may be unnecessary, e.g., for gas chromatography analysis.

It is possible that the remaining insoluble cellular debris will also be of interest, in which case one or more of the above-described separations will be followed by removal of substantially all liquid from the first compartment of the vessel, i.e., both aqueous and organic phases, followed by removal of the insoluble material which would then be subject to further purification or analysis.

In each of the above-described cases, it is further noted that, when more than one component is to be separated sequentially, it may be desirable to employ a clean filter after each component is isolated. Thus, for example, when using the vessel assembly of the instant invention, after one component has been separated from the liquid phase, the original filter tube may be removed and a new filter tube inserted in its place before the next component to be isolated is precipitated. Suitable filters for use in this invention include, e.g., those having pore sizes in the range of about 1–5 $\mu$m to achieve conveniently short filtration times, e.g., less than about 2 min; however, larger or smaller pore sizes can be used, e.g., where shorter or longer times are desired or tolerable and/or where efficient filtration is still achieved.

Each of the modifications of the method of this invention, as described for the separation of nucleic acids, which may be required to use this method for these other above-described uses will be evident to one of ordinary skill in the art, and will require only routine experimentation and optimization of fully conventional techniques.

A second aspect of this invention is a vessel particularly suitable for performing the process of this invention.

Referring now to FIGS. 1A and 1B, there is shown a double-ended extraction vessel, designated generally by the numeral 10, having a first end 11 and a second end 12. The extraction vessel 10 is preferably made from an injection-molded plastic such as polypropylene which is inert to the tissue samples and processing chemicals employed in the practice of the invention. A temporary cap 13 plugs the first end 11 of the vessel 10 when the vessel is used as a sample transport or storage container in order to keep moisture and foreign contamination from entering the first end 11 of the vessel. Approximately midway between the first and second ends 11 and 12 of the vessel 10 is a partition 14 which has a smooth surface 15 and a first roughened surface 16 comprised of a series of serrations. Extending through the partition 14 is a plurality of holes 17 which permit fluid communication between a first chamber 18 of the vessel 10 and a second chamber 19 of the vessel. The holes 17 provide coarse filtration.

Figure 4:
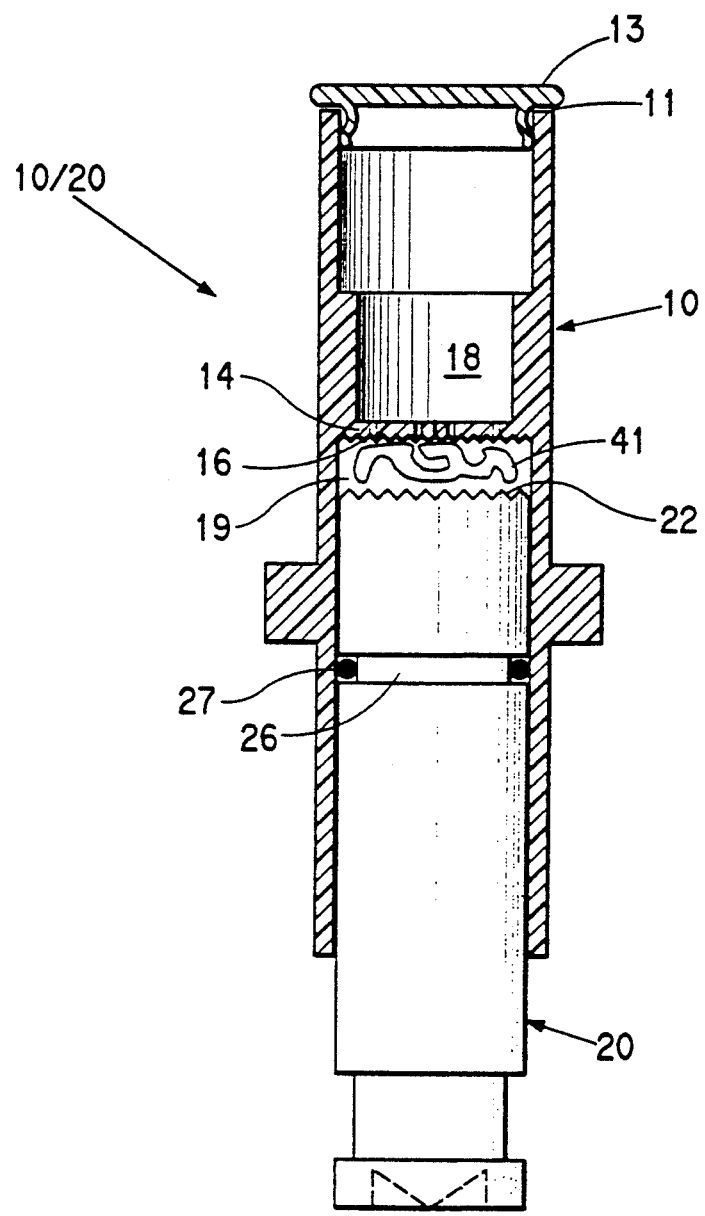
FIG. 4 is a side section view of a vessel assembly showing the extraction vessel of FIG. 1A in combination with the grinder-plunger of FIG. 2A.

Referring now to FIGS. 2A, 2B and 2C there is shown a grinder-plunger 20 which can be made of the same material, e.g., polypropylene, as the vessel 10 of FIG. 1A. Grinder-plunger 20 has a second roughened surface 22 at one end and a pair of indentations 25 at the opposite end. The indentations 25 provide a clutch for engagement with a rotational drive means (discussed in FIG. 6) which rotates the grinder-plunger 20 within the vessel 10 (FIG. 1A) to grind tissue to be analyzed against the serrated surface 16 on partition 14 of vessel 10. A groove 26 is disposed in the shank of grinder-plunger 20 for receiving an O-ring 27, which sealingly engages with the inner wall of chamber 19 when assembled with the vessel 10 as seen in FIG. 4. The seal also acts to retain the grinder-plunger 20 in chamber 19.

Figure 3A:
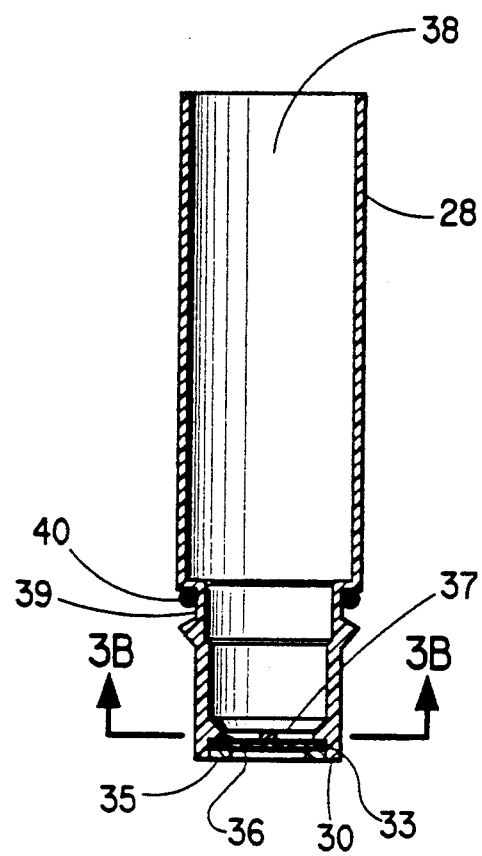
FIG. 3A is a sectional view taken along lines 3A—3A of FIG. 3B of a filter tube which is assembled with the extraction vessel of FIG. 1A during practice of the instant invention.
Figure 3B:
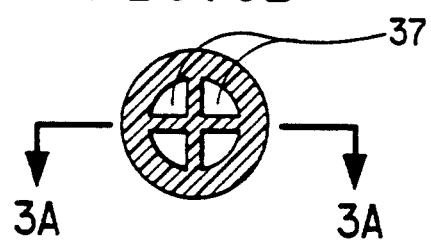

Referring now to FIG. 3A and 3B, a filter tube 28 is shown, which again is preferably made from injection molded plastic such as e.g., polypropylene and is similar to the filter tube described in U.S. Pat. No. 4,800,020, incorporated herein by reference. Other similar filtration devices are described in U.S. Pat. Nos. 4,454,231, 4,456,690, 4,310,058 and 4,587,221. Filter tube 28 slides into the upper chamber 18 of the double-ended vessel 10 of FIG. 1A as is shown in FIG. 5. Proximate its bottom end 30, the filter tube 28 has a filter element 33 which has at least one layer of foramenous material providing a selected porosity. Filter element 33 is held tightly against partition 36 to avoid any leakage there around which might provide pathways with openings of a greater diameter than the porosity of the filter. A ring 35 is secured to the end 30 of the filter tube 28 to hold the filter element 33 in position against partition 36 shown in FIG. 3A. The partition 36 has openings 37 therethrough that permit fluid communication between the filter element 33 and the interior barrel 38 of the filter tube 28. An O-ring groove 39 provides a seat for an O-ring 40 which seals against the interior wall 18 of the double-ended vessel 10 as is shown in FIG. 5.

Major components of the system comprising the double-ended vessel 10 (FIG. 1) the grinder-plunger 20 (FIG. 2) and the filter tube 28 (FIG. 3) have thus far been structurally described. These structural elements interact as set forth in FIGS. 4, 5 and 6.

Referring now to FIG. 4 the tissue sample 41 from which DNA is to be extracted is disposed within the chamber 19 of the double-ended vessel 10 for storage and transport. The tissue sample may be in a fresh or dried state e.g., a freeze-dried leaf sample from a corn plant. Sample 41 is retained within chamber 19 by inserting the grinder-plunger 20 into the chamber 19. The O-ring 27 provides a tight seal and frictionally retains grinder-plunger 20 in place so as to sandwich the sample 41 between serrated surfaces 16 and 22 of the partition 14 and the grinder-plunger 20 respectively. Freeze-drying of the tissue sample 41 is preferably carried out in a conventional manner with the sample stored in the double-ended vessel 10 and the cap 13 removed. To avoid contamination of the sample 41 subsequent to the freeze-drying step, cap 13 is replaced after freeze-drying.

Figure 6:
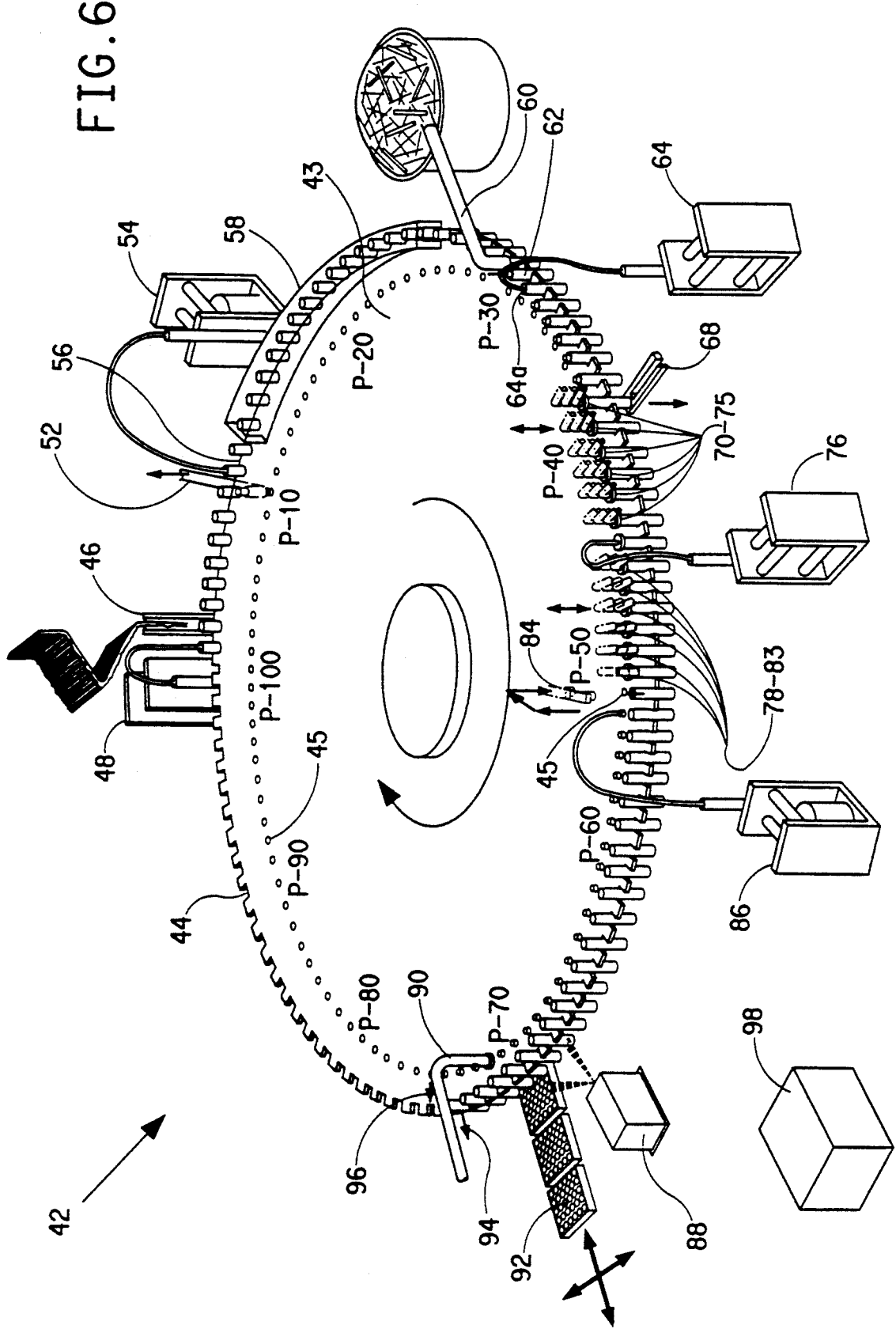
FIG. 6 is a perspective view of an apparatus which sequentially processes a multiplicity of the devices set forth in FIGS. 1-5 to automatically extract nucleic acids from the tissue samples.

Referring now to FIG. 5, the filter tube 28 is shown in assembly with the double-ended vessel 10 and the grinder-plunger 20, a step which occurs in the apparatus of FIG. 6. As will be explained hereinafter, extraction of the DNA is accomplished by moving the grinder-plunger 20 up and the filter tube 28 down in order to force a solution within the chamber 19 containing the DNA to be analyzed into the barrel 38 of the filter tube 28 from which it is eventually removed for analysis.

A third aspect of this invention is the process as described above performed in conjunction with the vessel as described above, in order to provide a reliable automated method of extracting, e.g., nucleic acids from large numbers of samples in a rapid, reproducible, essentially error-free way, by allowing the various steps of the process to all be performed within a single extraction vessel from the time of removal of the sample from its natural environment, through storage, to the preparation of isolated cellular component such as nucleic acid, and thus avoiding manual handling, transfer, centrifugation and other time-consuming and error-inducing steps.

Referring now to FIG. 6, referring, as exemplary, to the use of this invention to obtain nucleic acid samples, there is shown an apparatus, designated generally by the numeral 42, which provides an automated DNA extraction system utilizing the components of FIGS. 1, 2, and 3 in accordance with the principles of the instant invention. The apparatus 42 comprises a rotary indexing table 43 with multiple sample holding positions around its periphery. In the illustrated embodiment, there are 100 positions referred to as P-1 to P-100 and numbered at every tenth position. Each sample holding position contains a double-ended vessel port 44 and a filter-tube port 45. The turntable 43 indexes one position at a time and dwells at a position for about 1 minute during which time, the sample 41 (See FIGS. 4 and 5) is processed.

Surrounding the turntable 43 are the following processing devices disposed at various processing stations: vessel inserter 46, buffer injector 48, actuator 52 for the grinder-plunger 20, solvent injector 54, plunger mixer 56, filter tube inserter 60, filter plunger 62, precipitant injector 64, grinder-plunger extractor 68, pressure injectors 70-75, wash injector 76, pressure injectors 78-83, filter tube extractor 84, solvent injector 86, barcode reader 88, pressure injector 90, microtiter dish table 92, vessel remover 94, and filter tube remover 96. A controller 98, in communication with the aforementioned devices, device mounted sensors, and the turntable 43, coordinates the different activities in the process utilizing standard controller technology. Coordination of various steps utilizing the articles of FIGS. 1, 2, and 3 in combination with the assemblies of FIGS. 4 and 5 by utilizing the apparatus of FIG. 6 will now be explained.

As has been previously stated, while in the field, the sample 41 is retained in the double-ended vessel 10 by grinder-plunger 20 at which time a bar code I.D. is applied to the exterior of double-ended vessel.

When the double-ended vessel 10 arrives at the lab and is ready for processing, an operator removes the cap 13 from the vessel assembly 10/20 of FIG. 4 comprising the double-ended vessel 10 and grinder-plunger 20. The vessel assembly of FIG. 4 is then placed in the magazine of the vessel inserter 46. Inserter 46 places one vessel assembly in each port 44 as the turntable 43 indexes with the grinder-plunger end 21 oriented down as shown in FIG. 2A. In the illustrated example, vessel assembly 10/20 minus cap 13 is inserted at the vessel port 44 adjacent position P-1 and buffer injector 48 injects about 3 milliliters of CTAB into the now open chamber 18 of the vessel assembly 10/20 to rehydrate the tissue sample 41, if the tissue sample was freeze-dried, and to act as a buffer in later processing steps. The index positions P-2 – P-7 provide time for the sample 41 to rehydrate if necessary. At position P-8, grinder-plunger actuator 52 pushes the grinder up and squeezes the sample 41 between the roughened surface 16 on partition 14 in vessel 10 and the roughened surface 22 on the grinder-plunger 20. Drive pins on the actuator 52 engage the wedge-shaped indentations 25 on the grinder-plunger end 21 so as to rotate the grinder-plunger and grind the sample 41 between the serrated surfaces.

At position P-9, a solvent injector 54 injects about 0.4 milliliters of organic solvent, e.g., chloroform, into the open end 11 of the vessel 10. While at position P-9, the grinder-plunger mixer 56 engages the grinder-plunger 20 at slot 25A and reciprocates the grinder-plunger back and forth in the vessel 10 to mix the sample 41 in the solvent dispensed by injector 54. When mixing is complete, the grinder-plunger 20 is in the down position and the solution is in the lower chamber 19 of the vessel 10.

At position P-10, the assembly 10/20 enters the heater 58 where the tissue sample 41 remains through position P-25 so as to reach an equilibrium temperature of approximately 65° C. Settling and cooling of the tissue sample 41 occurs at positions P-26 – P-30.

At position P-31, the filter tube inserter 60 for the filter tube 28 of FIG. 3 removes a single filter tube from a magazine or a vibratory feeder and places it in the chamber 18 of the vessel 10 so as to provide the assembly 10/20/28 shown in FIG. 5. At position P-32, the filter plunger 62 pushes the filter tube 28 slowly down into the upper chamber 18 of the vessel 10 thereby forcing the solution through the filter 33, separating the solution from debris of the tissue sample 41 by leaving the organic solvent and cellular debris on the side of the filter adjacent the ring 35.

At position P-33, a precipitant injector 64 injects about 2.0 milliliters of a precipitant, e.g., isopropanol, into the open ended barrel 38 of the filter tube 28. The isopropanol causes the DNA in the solution to precipitate out of the solutions, The precipitant injector nozzle 64A is used to jet mix the precipitant dispensed by injector 64 thoroughly in the solution. During the time the vessel assembly indexes through positions P-34 – P-38, precipitate forms and settles onto the upper side of filter 33. At position P-39, the grinder-plunger extractor 68 pulls the grinder-plunger 20 down out of the vessel 10 by engaging the slot 25a at the lower end of the grinder-plunger 20. The grinder-plunger 20 is then discarded. Precipitate, in conjunction with the small porosity of the filter 33, keeps most of the liquid in the barrel 38 of filter tube 28.

At positions P-40-45, pressure injectors, 70–75 successively engage the barrel 38 of the filter tube 28 and apply pressure progressively to force the liquid through the precipitate and filter. The precipitate is left deposited on the upper surface of the filter 33.

At position P-46, the wash injector 76 injects about 6.0 milliliters of ethanol into the barrel 38 of the filter tube 28 and at positions P-47 – P-52, pressure injectors 78–73 successively register with the barrel 38 of the filter tube 28 and apply pressure to progressively force the liquid dispensed by wash injectors 76 through the precipitate and filter 33 to wash solution residue from the precipitate and filter.

At position P-53, the filter tube extractor 84 pulls the filter tube 28 from the vessel 10 and places it in the filter tube port 45 on the turntable 43 radially adjacent to vessel 10 and vessel port 44 from which it has been removed.

At position P-52, the solvent injector 86 injects about 0.5 milliliters of a nucleic acid solvent, e.g., Tris-EDTA, to dissolve the DNA in the washed precipitate which is on the back side of the filter 33. At positions P-53 – P-70, the filter tube 28 remains undisturbed and the solvent slowly dissolves the precipitate. The surface tension of the solution prevents the solution from flowing through the small pore of filter 33.

At position P-67, bar code reader 88 reads the bar code on the empty vessel 10 directly opposite the sample in the filter tube 28 and relays this information to the controller 98 by conventional means.

At position P-70, the pressure injector 90 registers with barrel 38 and the filter tube 28 and applies sufficient pressure to force the fluid in which the precipitant is now completely dissolved through the filter 33 and into a microtiter dish on indexable table 92. Forcing the solution through the filter 33 ensures that all of the sample precipitant on the upper surface of the filter is dissolved, so a high yield of DNA from the sample is assured. The microtiter dish positioner 92 positions the appropriate microtiter dish under the filter tube 28 and the sample is discharged into the dish under the control of controller 98. The bar code reader reads the bar code on the microtiter dish in the indexable table 92 and by using conventional methods, keeps track of samples in the control 98.

At position P-72, the vessel 10 is removed from the double end vessel port 44 of the turntable 43 and discarded. At position P-73, the filter tube 28 is removed from the filter tube port 45 of the turntable 43 and discarded.

In order to provide for expansion of the process or extending process times during the development of the DNA extraction system, positions P-74 – P-100 are provided in the turntable 43. Turntable 43 indexes in one minute time intervals so the process of extracting the DNA takes about 72 minutes from start of the process until the DNA is in the microtiter dish on table 92. From there, the DNA can be replicated and analyzed to determine the sample characteristics. Time to extract the DNA utilizing the automated apparatus of FIG. 6 in combination with the vessel system FIGS. 1–5 is substantially less than that required in previous manual methods employed. Moreover, the system is inherently reliable and precise for each sample so that the maximum yield of DNA is achieved without sample mixup or loss.

Without further elaboration, it is believed that one skilled in the art can, using the preceding description, utilize the present specific embodiments which are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications if any, cited above and below, are hereby incorporated by reference.

EXAMPLES

EXAMPLE 1

Purification of DNA

The following purification was performed using plant leaf tissue and the vessel assembly shown in FIG. 5. Two samples each of lyophilized maize were prepared.

0.11 g maize were placed in the lower chamber of the extraction vessel. The plunger was fitted into the lower chamber of the extraction vessel. Since the maize was lyophilized, the leaf sample was rehydrated by adding 4 ml of the CTAB Extraction Buffer and the plunger was withdrawn so that the leaf sample could soak in the lower chamber for 5 minutes. The sample was ground by pushing the plunger all the way into the lower chamber and rotating in a single direction for 45 seconds. Chloroform (0.4 ml) was added and quickly mixed by pulling the plunger down and pushing it up into the lower chamber for 2 cycles ending with the liquid in the lower chamber. The vessel assembly was immediately immersed in a 65° water bath such that one inch was above the water surface. After heating for 15 minutes, the vessel was removed from the bath and the plunger was pushed all the way into the lower chamber to force the liquid into the upper chamber. The vessel was allowed to sit undisturbed for 5 minutes. Next, the Uniprep filter unit (filter assembly consisting of filter membranes; 149 micron polypropylene, 1.2 micron nylon, 1.6 micron glass fiber, 149 micron polypropylene, in order from the filter barrel side of the filter to the open side of the filter) was pushed into the upper chamber while holding the plunger firmly against the wall between chambers. The Uniprep was removed from the vessel and the volume of filtrate measured. To precipitate the nucleic acids, isopropanol was added at a volume of 0.7 times that of the filtrates. The filtrate volume was 2 ml, and the volume of isopropanol added was 1.4 ml. The sample was mixed by pipetting up and down to form a homogeneous solution and allowed to sit at room temperature (21° C.) for 15 minutes.

At the end of the precipitation time, air pressure (40 psi) was applied to the top of the Uniprep barrel in order to force the liquid through the filter. The Uniprep barrel was filled with 6 ml of 70% ethanol, 30% water solution. This solution was forced through the filter under air pressure the same as with the precipitate, to wash the filter and precipitate.

To elute the nucleic acid from the filter, 0.25 ml TE (10 mM Tris-Cl, pH 7.5, 0.1 mM NaEDTA) was added within the barrel of the Uniprep filter and allowed to soak at room temperature (21° C.) for 20 minutes. To collect the eluted DNA, TE was forced through the filter under air pressure (20 psi) and collected as it emerged from the bottom of the Uniprep.

EXAMPLE 2

Purification of DNA

The following purifications were performed using plant leaf tissue and the DNA vessel assembly shown in FIG. 5. Two samples each of lyophilized maize, fresh soybean and lyophilized rice were prepared.

Maize, rice (0.11 grams per sample) and soybean (0.5 grams per sample) were placed in the lower chamber of the extraction vessel. The plunger was fitted into the lower chamber of each sample. Since maize and rice were lyophilized, the leaf samples were rehydrated by adding 4 ml of the CTAB Extraction Buffer and the plungers were withdrawn so that the leaf samples could soak in the lower chamber for 5 minutes. Soybean, being fresh, was ground before the buffer was added. All samples were ground in the same manner by pushing the plunger all the way into the lower chamber and rotating in a single direction for 45 seconds. At this point, 4 ml of CTAB Extraction Buffer was added to the soybean samples. Chloroform (0.4 ml) was added to all samples at the same time and quickly mixed by pulling the plunger down and pushing it up into the lower chamber for 2 cycles ending with the liquid in the lower chamber. The vessels were immediately immersed in a 65° water bath such that one inch was above the water surface. After heating for 15 minutes, the vessels were removed from the bath and the plungers were pushed all the way in to the lower chamber to force the liquid into the upper chamber. The vessels were allowed to sit undisturbed for 5 minutes. Next, the Uniprep filter units as in Example 1 (filter assembly consisting of filter membranes; 149 micron polypropylene, 1.2 micron nylon, 1.6 micron glass fiber, 149 micron polypropylene, in order from the filter barrel side of the filter to the open side of the filter) were pushed into the upper chamber while holding the plunger firmly against the wall between chambers. The Unipreps were removed from the vessel and the volume of filtrate measured. To precipitate the nucleic acids, isopropanol was added at a volume of 0.7 times that of the filtrates. The filtrate volumes for sample #1 Maize, #2 Maize, #3 Soybean, #4 Soybean, #5 Rice and #6 Rice were, respectively 2 ml, 1.5 ml, 1.7 ml, 1.6 ml, 1.5 ml, 1.1 ml. Isopropanol volumes were, respectively, 1.4 ml, 1.0 ml, 1.2 ml, 1.2 ml, 1.0 ml, 0.8 ml. The samples were mixed by pipetting up and down to form a homogeneous solution and allowed to sit at room temperature (21° C.) for 15 minutes (samples 1 and 2), 5 minutes (samples 3 and 4), 10 minutes (samples 5 and 6).

At the end of the precipitation time, air pressure (40, 60, 50, 45, 50, 50 psi for samples 1-6, respectively) was applied to the top of the Uniprep barrels in order to force the liquid through the filters and trap the nucleic acid precipitate on the filter. Each Uniprep barrel was filled with 6 ml of 70% ethanol, 30% water solution. This solution was forced through the filter under air pressure the same as with the precipitate, to wash the filter and precipitate.

Figure 7:
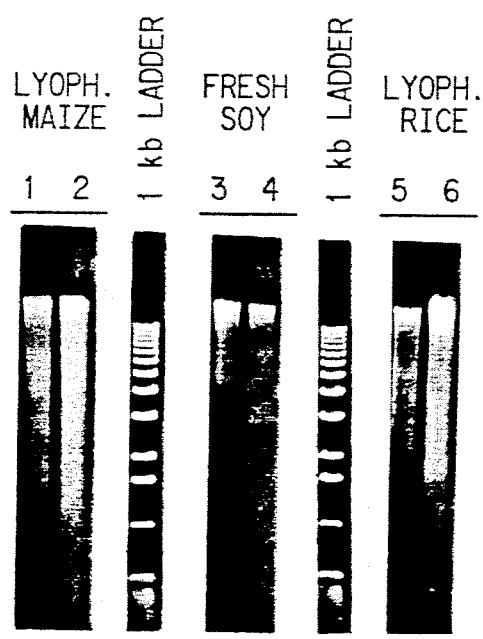
FIG. 7 is an analysis of the DNA preparations by agarose gel electrophoresis.

To elute the nucleic acid from the filter, 0.25 ml TE (10 mM Tris-Cl, pH 7.5, 0.1 mM NaEDTA) was added within the barrel of the Uniprep filter and allowed to soak at room temperature (21° C.) for 20, 20, 10, 10, 20 and 20 minutes for samples 1-6, respectively. To collect the eluted DNA, TE was forced through the filters under air pressure (20 psi) and collected as it emerged from the bottom of the Uniprep. The yield and quality of the DNA product was analyzed as described in FIG. 7.

Gel Electrophoresis: 15 $\mu$l of each DNA preparation from Example 2 was dried under vacuum (Speed Vac; Savant Corp.) and dissolved in 15 $\mu$l of deionized water. 1 $\mu$l of RNAase A (1 mg/ml water) was added to each sample and the samples were incubated at 21° C. for 10 min. 1 $\mu$l sodium dodecylsulfate (1.5% in water) was added to each sample and the samples were incubated at 65° C. for 5 min. The samples were mixed with 4 $\mu$l of Stop Buffer (0.17% bromophenol blue, 0.17% xylene cyanol, 33% glycerol, 83 mM NaEDTA and were electrophoresed on 0.8% agarose gel according to common practice (J. Sambrook, E.F. Fritsch and T. Maniatis, eds. (1989) *Molecular Cloning: A Laboratory Manual*, Cold Spring Harbor Laboratory Press, Cold Spring Harbor, NY, pp. 6.3-6.9) The DNA samples are as indicated. Determination of total nucleic acids: 10 $\mu$l of each DNA sample was added to 390 $\mu$l of TE and the optical absorbance at 260 nm was measured. The total yield of nucleic acid in each sample was calculated using a conversion factor of 40 $\mu$g/ml per absorbance unit. Determination of DNA: The total amount of DNA in each sample was determined by analysis with diphenylamine (K.W. Giles and A. Myers. 1965. Nature 206:93-100).

EXAMPLE 3

Amplification of Maize DNA Using a Thermostable DNA Polymerase (Described in Lassnet e al., supra.)

Maize DNA was prepared as described in Example 1. A cocktail consisting of the ingredients for amplification was prepared by mixing 353 $\mu$l of water, 45 $\mu$l of the 10× reaction buffer specified in the brochure accompanying Amplitaq polymerase (Cetus Corp), 7.2 $\mu$l of 0.25 M MgCl$_2$, 6.75 $\mu$l of the oligodeoxynucleotide primer 5'-GCAAGTAGCT (10 $\mu$M stock solution), 36

μl of a solution consisting of 1.25 mM each of dATP, dCTP, dGTP and dTTP, and 1.8 ∝l of Amplitaq polymerase (5000 units/ml; Cetus Corp). A series of wells in a polyvinylchloride microtiter plate (Falcon #3911) were filled with 50 μl of the above cocktail, except that 75 μl was placed in the first well of the series. Ten microliters of maize DNA was heated at 99° C. for 3 minutes, and 7 μl of this was added to 75 μl of cocktail in the first well. Twenty-five μl of the contents of the first well were transferred to the second well; 25 μl were transferred to the second well, and so on, to produce a series of eight 3-fold dilutions of the DNA in the cocktail. Empty wells in the microtiter plate were filled with 50 μl of water. Every sample well was overlayed with 40 μl of mineral oil and the microtiter plate was placed in a Biocycler oven (Bios Corp.). The oven was programmed for 35 cycles with the thermal profile 94° for 1 minute, 35° for 30 seconds, ramp to 72° in 2 minutes, 72° for 2 minutes. Twelve μl of Stop Buffer (supra) was added to each sample and 15 μl of each was electrophoresed in a 1.4% agarose gel according to common practice (J. Sambrook et al., supra).

Figure 8:
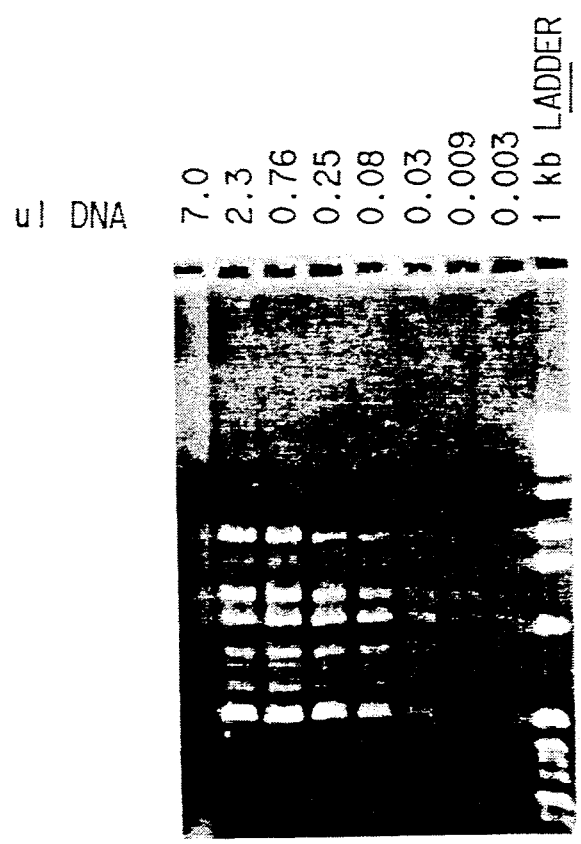
FIG. 8 is an agarose gel showing that DNA prepared by the process of this invention utilizing the vessel of this invention is suitable for amplification using Taq DNA polymerase.

The volume of the DNA preparation added to each 50 μl reaction mixture was calculated according to the dilution factor, and is indicated in FIG. 8. In this example, amplification of 0.8 μl of maize DNA was sufficient for visualization of amplified DNA segments in the ethidium bromide-stained gel. Since the DNA preparation is in a volume of 250 μl, a total of 250/0.08 or 3125 separate amplification reactions could be performed on the DNA from a single preparation.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A device useful for storing, transporting and processing a biological sample from which solvent soluble components in a fluid are extracted, comprising:

an extraction vessel having an upper chamber and a lower chamber, the chambers being separated by a radially extending wall having an upper surface and a lower surface and means for allowing fluid to pass therethrough, a plunger having an end surface for insertion into the lower chamber; and a plurality of serrations formed on the lower surface of the radially extending wall and on the inserted opposing end surface of the plunger for disrupting a biological sample upon relative movement between the plunger and the extraction vessel, whereby solvent soluble components are released from the biological sample.

2. The device of claim 3, further comprising a tube having a barrel, the tube being insertable into the upper chamber for accumulating the fluid introduced therein from the lower chamber, the tube further including means for separating the soluble components from the insoluble components in said fluid after transfer of the fluid from the lower chamber into the upper chamber, and means for sealing between the tube and the upper chamber to block fluid communication through the upper chamber.

3. The device of claim 2, wherein the means for separating the insoluble components in said fluid is a filter.

4. The device of claim 3, wherein the plunger means includes a slot and further wherein the slot is engagable by means for reciprocating the plunger means axially to move the plurality of serrations in and out of proximity with one anther and to push fluid back and forth between the lower chamber and the upper chamber of the extraction vessel.

5. An apparatus for automatically extracting at least on solvent soluble component from at least one sample, the sample comprising solvent soluble components in a fluid and residual debris, the apparatus comprising:

(a) an extraction vessel assembly including:

(i) an extraction vessel having an upper chamber and a lower chamber, the upper and lower chambers being separated by a radially extending wall having an upper surface and a lower surface and a plurality of holes formed therein for allowing fluid to pass from the lower chamber to the upper chamber, (ii) a plunger having an end insertable into the lower chamber, and (iii) a tube having a barrel, the tube having an end being insertable into the upper chamber for accumulating the fluid introduced therein from the lower chamber, the tube including a filter for separating the soluble components from the insoluble components in the fluid after the transfer of the fluid from the lower chamber to the upper chamber;

(b) a turntable having a plurality of sample holding positions circumferentially distributed therearound, each sample holding position having an extraction vessel port for receiving an extraction vessel and a tube port disposed in radial alignment with the extraction vessel port for receiving a tube;

(c) a vessel inserter for inserting the extraction vessel assembly into each extraction vessel port;

(d) an actuator for pushing the plunger up and squeezing the sample between the lower surface of the radially extending wall and the upper surface of the plunger, thereby releasing the debris and the fluid from the sample;

(e) a tube inserter for inserting the tube into the upper chamber of the extraction vessel assembly;

(f) a tube extractor for removing the tube from the vessel assembly and placing it into the tube port;

(g) an array of microtiter dishes disposed on an indexable table located below the turntable;

(h) a vessel remover for removing the extraction vessel assembly from each extraction vessel port; and (i) a tube remover for removing the tube from each tube port.

6. The apparatus of claim 5, further comprising:

(j) a buffer injector for injecting a buffer into the upper chamber of the extraction vessel;

(k) a solvent injector for injecting a first solvent into the upper chamber of the extraction vessel;

(l) a plunger mixer for engaging the plunger at a slot formed in the plunger and for reciprocating the plunger to mix the sample in the solvent to form a first solution;

(m) a filter plunger for pushing the filter disposed in the tube into the upper chamber of the extraction vessel, thereby forcing the first solution through the filter and separating the first solution from the debris of the sample;

(n) a precipitant injector for injecting a precipitant into the tube for causing a substance in the first solution to precipitate out of the first solution, thereby forming a precipitate;

(o) a plunger extractor for pulling the plunger out of the extraction vessel assembly by engaging the slot in the plunger;

(p) a plurality of first pressure injectors disposed in engagement with the barrel of each tube for applying pressure progressively to force the first solution through the precipitate and the filter;

(q) a plurality of wash injectors for injecting wash fluid into each tube;

(r) a plurality of second pressure injectors disposed in registry with each tube for applying pressure to progressively force the wash fluid through the precipitate;

(s) a solvent injector for injecting a second solvent to dissolve the substance in the washed precipitate and to form a second solution;

(t) a bar code reader for reading a bar code on each extraction vessel;

(u) a third pressure injector disposed in registry with a respective tube for applying sufficient pressure to the second solution to force the second solution through the filter and into a respective microtiter dish; and (v) a controller for controlling the operation of elements (c) – (u) and for receiving the bar code information.

* * * * *